(12) United States Patent
Nevo

(10) Patent No.: US 8,193,147 B2
(45) Date of Patent: Jun. 5, 2012

(54) USE OF COPOLYMER 1 FOR TREATMENT OF MUSCULAR DYSTROPHY

(75) Inventor: Yoram Nevo, Tel Aviv (IL)

(73) Assignee: Hadasit Medical Research Services & Development Ltd., Jerusalem (IL)

( * ) Notice: Subject to any disclaimer, the term of this patent is extended or adjusted under 35 U.S.C. 154(b) by 0 days.

(21) Appl. No.: 12/679,866

(22) PCT Filed: Sep. 24, 2008

(86) PCT No.: PCT/IL2008/001289
§ 371 (c)(1),
(2), (4) Date: Nov. 8, 2010

(87) PCT Pub. No.: WO2009/040814
PCT Pub. Date: Apr. 2, 2009

(65) Prior Publication Data
US 2011/0053853 A1    Mar. 3, 2011

Related U.S. Application Data

(60) Provisional application No. 60/974,591, filed on Sep. 24, 2007.

(51) Int. Cl.
*A61K 38/00* (2006.01)
*A61K 31/56* (2006.01)
*A61K 31/20* (2006.01)
*A61K 31/16* (2006.01)

(52) U.S. Cl. .......... 514/1.1; 514/171; 514/560; 514/613

(58) Field of Classification Search .................... 514/1.1, 514/171, 560, 613
See application file for complete search history.

(56) References Cited

U.S. PATENT DOCUMENTS

| 6,214,791 B1 | 4/2001 | Arnon et al. |
| 6,844,314 B2 | 1/2005 | Eisenbach-Schwartz et al. |

FOREIGN PATENT DOCUMENTS

| WO | WO 2001052878 A2 | 7/2001 |
| WO | WO 2001093893 A2 | 12/2001 |
| WO | WO 2003047500 A2 | 6/2003 |
| WO | WO 2004060265 A2 | 7/2004 |
| WO | WO 2005046719 A1 | 5/2005 |
| WO | WO 2006057003 A2 | 6/2006 |

OTHER PUBLICATIONS

Manzur AY, Kuntzer T, Pike M, Swan A. Glucocorticoid corticosteroids for Duchenne muscular dystrophy. Cochrane Database Syst Rev. 2004.
Richard M. Keeling, Paul T. Golumbek, Elizabeth M. Streif, Anne M. Connolly Weekly Oral Prednisolone Improves Survival and Strength in Male Mdx Mice. Muscle and Nerve 2007.

*Primary Examiner* — Raymond Henley, III
(74) *Attorney, Agent, or Firm* — Browdy and Neimark, PLLC

(57) ABSTRACT

The invention provides an active agent selected from the group consisting of Copolymer 1, a Copolymer 1 related-peptide and a Copolymer 1-related polypeptide, or a pharmaceutically acceptable salt thereof, and pharmaceutical compositions comprising the active agent, for use in treating a muscular dystrophy disease or disorder.

14 Claims, 5 Drawing Sheets

USE OF COPOLYMER 1 FOR TREATMENT OF MUSCULAR DYSTROPHY

FIELD OF THE INVENTION

The present invention relates to methods and compositions for treatment of muscular dystrophy diseases or disorders and, in particular, to such methods and compositions comprising Copolymer 1.

BACKGROUND OF THE INVENTION

Muscular dystrophy refers to a group of genetic, hereditary muscle diseases and disorders that cause progressive muscle weakness. These diseases and disorders are characterized by progressive skeletal muscle weakness, defects in muscle proteins, and the death of muscle cells and tissue. Many different diseases including Duchenne, Becker, limb girdle, congenital, facioscapulohumeral, myotonic, oculopharyngeal, distal, and Emery-Dreifuss are classified as muscular dystrophies.

Duchenne muscular dystrophy is the most common form of muscular dystrophy and primarily affects boys.

Mutations of the membrane-associated proteins dystrophin and merosin result in progressive muscle wasting and weakness in Duchenne and congenital muscular dystrophy, respectively (Dalkilic, 2003; Tidball, 2005). Boys with Becker muscular dystrophy (very similar to but less severe than Duchenne muscular dystrophy) have faulty or diminished amount of dystrophin. Following muscle plasma membrane damage during contraction, muscle injury produces dysregulation of a broad spectrum of structural and regulatory genes which accompany muscle fiber death (Petrol et al., 1993; Tidball, 2005; Ge et al., 2004). Interestingly, while initial even severe muscle degeneration results in extremely effective regeneration in cases of rhabdomyolysis, recurrent muscle injury in muscular dystrophy is associated with failure of regeneration and replacement of the muscle tissue with fibrous tissue (fibrosis) and fat.

The laboratory of the present inventor is interested in the pathophysiology of muscular dystrophy and the inter-relationship and interaction between fibrosis and regeneration in these muscular dystrophies (Nevo et al., 2006; Biton et al., 2006) and looks for the development and implementation of therapeutic modalities that will inhibit muscle inflammation and fibrosis and enhance regeneration in muscular dystrophy patients.

Inflammation in Muscular Dystrophy

Inflammatory process plays a major role in promoting the pathology of dystrophin-deficient muscle (Morrison et al., 2005). The degeneration of muscle fibers is accompanied by invasion of inflammatory cells including macrophages, CD4+ and CD8+, T lymphocytes, IgG, IgM, and eosinophils (Spencer et al., 2001). In the mdx mouse model, T cells are reported to contribute significantly to apoptosis of skeletal muscle and progressive fibrinogenesis during repeated cycles of muscle degeneration (Morrison et al., 2000; Spencer et al., 2001). Mdx lymph node cells produced large amounts of INF-γ but not IL-4, IL-6 or IL-10 after in vitro mitogen stimulation with concanavalin A, especially during the regeneration phase of muscular dystrophy. INF-γ is a cytokine that up-regulates the expression of adhesion molecules, major histocompatibility complex (MHC) gene products and chemokines, which can ultimately stimulate an inflammatory reaction occurring in the muscle tissue (Matthys et al., 1999, 2001; Tran et al., 2000). However it is possible that INF-γ is also playing a protective role in the control of skeletal muscle inflammation and fibrosis in the mdx mice. INF-γ also participates as a direct B-cell-maturing cytokine, driving normal B cell to active Ig secretion.

In the mdx mice, depletion of macrophages prevents most muscle membrane lysis at the peak of pathology (Wehling et al., 2001). Implication for the participation of T cells in the process of fibrosis was demonstrated in experiments carried out in mdx mice with the nu/nu background. Transplantation of normal thymic tissue into mdx nu/nu mice replenished deposition of altered collagen in the muscular tissue comparable to wild-type mdx dystrophic mice (Morrison et al., 2000).

Copolymer 1—Glatiramer Acetate (GA)

Copolymer 1, first described in U.S. Pat. No. 3,849,550, is an FDA and Israel Ministry of Health approved drug for multiple sclerosis (MS) that slows the progression of disability and reduces relapse rate while exhibiting a very high safety profile. MS and its animal model, experimental autoimmune encephalitis (EAE), are inflammatory autoimmune diseases of the central nervous system (CNS) characterized by myelin destruction and axonal damage. Glatiramer acetate (GA), the trivial chemical name for the acetate salt of Copolymer 1, is composed of the amino acids L-alanine, L-lysine, L-glutamic acid, and L-tyrosine in a molar ratio of 4.2:3.4:1.4:1.0, and is marketed under the name Copaxone® (a trademark of Teva Pharmaceutical Industries Ltd., Petach Tikva, Israel). It was designed to simulate myelin basic protein (MBP). The immunological cross-reactivity with MBP was initially considered the cause for its activity.

Copolymer 1 and T cells activated thereby were also found to confer neuroprotection and to inhibit secondary neuronal degeneration caused by an injury, disease or disorder in the CNS and to protect CNS cells from glutamate toxicity (WO 01/52878, WO 01/93893, U.S. Pat. No. 6,844,314). In this context, Copolymer 1 was found to confer neuroprotection in animal models of amyotrophic lateral sclerosis (ALS) (WO 03/047500), Parkinson's disease and Alzheimer's disease (WO 2005/046719). Treatment with Cop 1 by ingestion or inhalation is disclosed in U.S. Pat. No. 6,214,791 and by eyedrops in WO 2004/060265.

GA exerts its therapeutic activity by immunomodulating various levels of the immune response, which differ in their degree of specificity. The prerequisite step is the binding of GA to MI-IC class II molecules. GA exhibited a very rapid, high, and efficient binding to various MI-IC class II molecules on murine and human antigen-presenting cells, and even displaced peptides from the MHC-binding site. This competition for binding to the MI-IC can consequently lead to inhibition of various pathological effector functions. It was shown that GA promotes T helper 2 (Th2) cell development and increase IL-10 production. This modulation on the level of antigen-presenting cells is the least specific step and can be beneficial for the modulation of detrimental immune responses to various antigens. (Aharoni et al., 1999, Putheti et al., 2003, Farina et al., 2005).

GA-immunomodulating activity is not limited to the brain. GA-induced Th2 regulatory cells were demonstrated in other organs (spleens and lymph nodes of experimental animals and peripheral blood mononuclear cells in humans). Moreover, as demonstrated in these studies, highly reactive GA-specific T cell lines secrete in vitro IL-4, IL-5, IL-10, and TGF-β in response to GA (Miller et al., 1998). In skin transplantation system, GA significantly prevented skin graft rejection. GA alleviates immune rejection and drastically reduced cytotoxic activity toward host targets in bone marrow transplantation (Aharoni et al., 1997; 2001).

Muscular dystrophy is not a primary inflammatory disorder. However, as previously shown the process of replacement of the normal muscle tissue by fibrosis in muscular dystrophy is mediated and enhanced by inflammation. There is no previous data on the effect of Copolymer 1 on muscular dystrophy.

Current Treatment of Muscular Dystrophy:

Corticosteroids are the only available medication with proven efficacy in Duchenne muscular dystrophy (DMD). In the short-term, corticosteroids significantly improve muscle strength and function in DMD (Manzur et al., 2004). Long-term corticosteroid treatment is associated with clinical benefit of improvement in muscle strength both in the mdx mice and in boys with DMD, prolonging their shortened lifespan and amelioration of scoliosis (Keeling et al., 2007). However, prolonged corticosteroid treatment is associated with severe side effects including obesity, hypertension, cataracts, bone fragility, behavior disturbances and others (Angelini, 2007). The mechanism of action of corticosteroids in muscular dystrophy is not entirely known. Corticosteroids have significant anti-inflammatory and immune modulation effect. Treatment of patients with dystrophies with corticosteroids reduces the mononuclear inflammatory cells (MICs), (Hussein et al., 2006) and the total T cells number (Kissel et al., 1993).

It would be highly desirable to provide medicaments for the treatment of DMD and other non-DMD muscular dystrophies for which no medication is presently available.

SUMMARY OF THE INVENTION

The present invention provides an active agent selected from the group consisting of Cop 1, a Cop 1 related-peptide and a Cop 1-related polypeptide, or a pharmaceutically acceptable salt thereof for use in treating a muscular dystrophy disease or disorder.

In one preferred embodiment, the active agent for use in the methods and composition of the invention is Copolymer 1, herein referred to also as Cop 1, most preferably in the form of its acetate salt known under the generic name glatiramer acetate.

In another preferred embodiment, the present invention further comprises use of an active agent or a pharmaceutically acceptable salt thereof in combination with at least one anti-inflammatory agent, such as a corticosteroid, a non-steroidal anti-inflammatory drug or colchicine.

The use or treatment according to the invention may also improve muscle strength and mobility, prevent or reduce muscle degeneration, fibrosis and/or spinal scoliosis, and prevent heart failure and respiratory failure in subjects with muscular dystrophies.

In one aspect, the present invention is directed to the use of an active agent selected from the group consisting of Cop 1, a Cop 1 related-peptide and a Cop 1-related polypeptide, or a pharmaceutically acceptable salt thereof for the preparation of a medicament for the treatment of a muscular dystrophy disease or disorder.

The invention further relates to methods and a pharmaceutical composition for treatment of a muscular dystrophy disease or disorder, comprising a therapeutically effective amount of an active agent selected from the group consisting of Cop 1, a Cop 1 related-peptide and a Cop 1-related polypeptide, or a pharmaceutically acceptable salt thereof.

DETAILED DESCRIPTION OF THE INVENTION

Figure 1A:
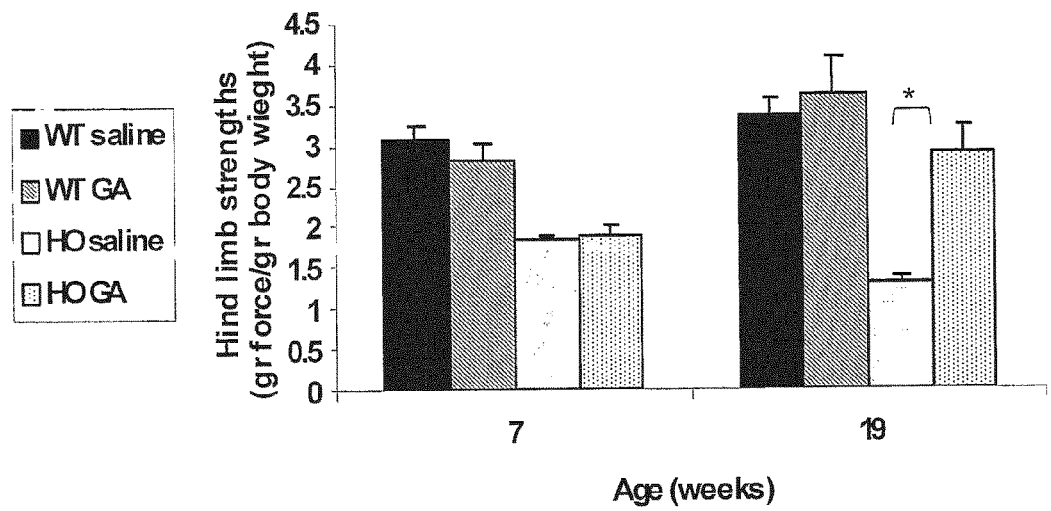
FIGS. 1A-1B shows muscle grip strength per body weight of the hind limbs (1A) and the fore limbs (1B) of WT (wild type) C57BL and HO (homozygote) $dy^{2j}$ mice in the glatiramer acetate (GA)-treated and untreated groups (n=5 for each group).

The present invention provides an active agent selected from the group consisting of Cop 1, a Cop 1 related-peptide and a Cop 1-related polypeptide, or a pharmaceutically acceptable salt thereof for use in treating a muscular dystrophy disease or disorder.

The active agent of this invention targets the secondary inflammatory process which is associated with muscle degeneration. Its effect is on downstream pathways of regeneration and fibrosis. Therefore this non-specific effect is not limited to a single muscular dystrophy but intends to counteract the "dystrophic changes", the common final pathway of various muscular dystrophies.

The terms "Cop 1" and Copolymer 1" are used herein interchangeably. For the purpose of the present invention, "Cop 1 or a Cop 1-related peptide or polypeptide" is intended to include any peptide or polypeptide, including a random copolymer, that cross-reacts functionally with myelin basic protein (MBP) and is able to compete with MBP on the MHC class II in the antigen presentation.

The active agent of the invention may comprise a random copolymer comprising a suitable quantity of a positively charged amino acid such as lysine or arginine, in combination with a negatively charged amino acid (preferably in a lesser quantity) such as glutamic acid or aspartic acid, optionally in combination with a non-charged neutral amino acid such as alanine or glycine, serving as a filler, and optionally with an amino acid adapted to confer on the copolymer immunogenic properties, such as an aromatic amino acid like tyrosine or tryptophan. Such compositions may include any of those copolymers disclosed in WO 00/05250, the entire contents of which being hereby incorporated herein by reference.

More specifically, the active agent for use in the present invention comprises at least one copolymer selected from the group consisting of random copolymers comprising one amino acid selected from each of at least three of the following groups: (a) lysine and arginine; (b) glutamic acid and aspartic acid; (c) alanine and glycine; and (d) tyrosine and tryptophan.

The copolymers for use in the present invention can be composed of L- or D-amino acids or mixtures thereof. As is known by those of skill in the art, L-amino acids occur in most natural proteins. However, D-amino acids are commercially available and can be substituted for some or all of the amino acids used to make the terpolymers and other copolymers used in the present invention. The present invention contemplates the use of copolymers containing both D- and L-amino acids, as well as copolymers consisting essentially of either L- or D-amino acids.

In one embodiment of the invention, the copolymer contains four different amino acids, each from a different one of the groups (a) to (d). A preferred copolymer according to this embodiment comprises in combination alanine, glutamic acid, lysine, and tyrosine, of net overall positive electrical charge and of a molecular weight of about 2,000-40,000 Da, preferably of about 2,000-13,000 Da, and is most preferably Copolymer 1 of average molecular weight of about 4,700-13,000 Da. Preferred molecular weight ranges and processes for making a preferred form of Cop 1 are described in U.S. Pat. No. 5,800,808, the entire contents of which being hereby incorporated in the entirety. It is clear that this is given by way of example only, and that the active agent can be varied both with respect to the constituents and relative proportions of the constituents if the above general criteria are adhered to. Thus, the copolymer may be a polypeptide from about 15 to about 100, preferably from about 40 to about 80, amino acids in length, and is preferably the copolymer having the generic name glatiramer acetate.

In another embodiment, the copolymer contains three different amino acids each from a different one of three groups of the groups (a) to (d). These copolymers are herein referred to as terpolymers.

In one embodiment, the terpolymers for use in the present invention contain tyrosine, alanine, and lysine, hereinafter designated YAK. The average molar fraction of the amino acids in these terpolymers can vary. For example, tyrosine can be present in a mole fraction of about 0.005-0.250; alanine can be present in a mole fraction of about 0.3-0.6; and lysine can be present in a mole fraction of about 0.1-0.5. The average molecular weight is between 2,000-40,000 Da, and preferably between about 3,000-35,000 Da. In a more preferred embodiment, the average molecular weight is about 5,000-25,000 Da. It is possible to substitute arginine for lysine, glycine for alanine, and/or tryptophan for tyrosine.

In another embodiment, the terpolymers for use in the present invention contain tyrosine, glutamic acid, and lysine, hereinafter designated YEK. The average molar fraction of the amino acids in these terpolymers can vary: glutamic acid can be present in a mole fraction of about 0.005-0.300, tyrosine can be present in a mole fraction of about 0.005-0.250, and lysine can be present in a mole fraction of about 0.3-0.7. The average molecular weight is between 2,000-40,000 Da, and preferably between, about 3,000-35,000 Da. In a more preferred embodiment, the average molecular weight is about 5,000-25,000 Da. It is possible to substitute aspartic acid for glutamic acid, arginine for lysine, and/or tryptophan for tyrosine.

In another embodiment the terpolymers for use in the present invention contain lysine, glutamic acid, and alanine, hereinafter designated KEA. The average molar fraction of the amino acids in these polypeptides can also vary. For example, glutamic acid can be present in a mole fraction of about 0.005-0.300, alanine can be present in a mole fraction of about 0.005-0.600, lysine can be present in a mole fraction of about 0.2-0.7. The average molecular weight is between 2,000-40,000 Da, and preferably between about 3,000-35,000 Da. In a more preferred embodiment, the average molecular weight is about 5,000-25,000 Da. It is possible to substitute aspartic acid for glutamic acid, glycine for alanine, and/or arginine for lysine.

In another embodiment, the terpolymers for use in the present invention contain tyrosine, glutamic acid, and alanine, hereinafter designated YEA. The average molar fraction of the amino acids in these polypeptides can vary. For example, tyrosine can be present in a mole fraction of about 0.005-0.250, glutamic acid can be present in a mole fraction of about 0.005-0.300, and alanine can be present in a mole fraction of about 0.005-0.800. The average molecular weight is between 2,000-40,000 Da, and preferably between about 3,000-35,000 Da. In a more preferred embodiment, the average molecular weight is about 5,000-25,000 Da. It is possible to substitute tryptophan for tyrosine, aspartic acid for glutamic acid, and/or glycine for alanine.

In a more preferred embodiment, the mole fraction of amino acids of the terpolymers is about what is preferred for Copolymer 1. The mole fraction of amino acids in Copolymer 1 is glutamic acid about 0.14, alanine about 0.43, tyrosine about 0.10, and lysine about 0.34. The most preferred average molecular weight for Copolymer 1 is between about 5,000-9,000 Da. The activity of Copolymer 1 for the composition disclosed herein is expected to remain if one or more of the following substitutions is made: aspartic acid for glutamic acid, glycine for alanine, arginine for lysine, and tryptophan for tyrosine.

The molar ratios of the monomers of the more preferred terpolymer of glutamic acid, alanine, and tyrosine, or YEA, is about 0.21 to about 0.65 to about 0.14.

The molar ratios of the monomers of the more preferred terpolymer of glutamic acid, alanine and lysine, or KEA, is about 0.15 to about 0.48 to about 0.36.

The molar ratios of the monomers of the more preferred terpolymer of glutamic acid, tyrosine, and lysine, or YEK, is about 0.26 to about 0.16 to about 0.58.

The molar ratios of the monomers of the more preferred terpolymer of tyrosine, alanine and lysine, or YAK, is about 0.10 to about 0.54 to about 0.35.

The terpolymers can be made by any procedure available to one of skill in the art. For example, the terpolymers can be made under condensation conditions using the desired molar ratio of amino acids in solution, or by solid phase synthetic procedures. Condensation conditions include the proper temperature, pH, and solvent conditions for condensing the carboxyl group of one amino acid with the amino group of another amino acid to form a peptide bond. Condensing agents, for example dicyclohexyl-carbodiimide, can be used to facilitate the formation of the peptide bond. Blocking groups can be used to protect functional groups, such as the side chain moieties and some of the amino or carboxyl groups against undesired side reactions.

For example, the process disclosed in U.S. Pat. No. 3,849,650, can be used wherein the N-carboxyanhydrides of tyrosine, alanine, γ-benzyl glutamate and N ε-trifluoroacetyl-lysine are polymerized at ambient temperatures in anhydrous dioxane with diethylamine as an initiator. The γ-carboxyl group of the glutamic acid can be deblocked by hydrogen bromide in glacial acetic acid. The trifluoroacetyl groups are removed from lysine by 1 molar piperidine. One of skill in the art readily understands that the process can be adjusted to make peptides and polypeptides containing the desired amino acids, that is, three of the four amino acids in Copolymer 1, by selectively eliminating the reactions that relate to any one of glutamic acid, alanine, tyrosine, or lysine. For purposes of this application, the terms "ambient temperature" and "room temperature" mean a temperature ranging from about 20 to about 26° C.

The molecular weight of the terpolymers can be adjusted during polypeptide synthesis or after the terpolymers have been made. To adjust the molecular weight during polypeptide synthesis, the synthetic conditions or the amounts of amino acids are adjusted so that synthesis stops when the polypeptide reaches the approximate length which is desired. After synthesis, polypeptides with the desired molecular weight can be obtained by any available size selection procedure, such as chromatography of the polypeptides on a molecular weight sizing column or gel, and collection of the molecular weight ranges desired. The present polypeptides can also be partially hydrolyzed to remove high molecular weight species, for example, by acid or enzymatic hydrolysis, and then purified to remove the acid or enzymes.

In one embodiment, the terpolymers with a desired molecular weight may be prepared by a process which includes reacting a protected polypeptide with hydrobromic acid to form a trifluoroacetyl-polypeptide having the desired molecular weight profile. The reaction is performed for a time and at a temperature which is predetermined by one or more test reactions. During the test reaction, the time and temperature are varied and the molecular weight range of a given batch of test polypeptides is determined. The test conditions which provide the optimal molecular weight range for that batch of polypeptides are used for the batch. Thus, a trifluoroacetyl-polypeptide having the desired molecular weight profile can be produced by a process which includes reacting the protected polypeptide with hydrobromic acid for a time and at a temperature predetermined by test reaction. The trifluoroacetyl-polypeptide with the desired molecular weight profile is then further treated with an aqueous piperidine solution to form a low toxicity polypeptide having the desired molecular weight.

In a preferred embodiment, a test sample of protected polypeptide from a given batch is reacted with hydrobromic acid for about 10-50 hours at a temperature of about 20-28° C. The best conditions for that batch are determined by running several test reactions. For example, in one embodiment, the protected polypeptide is reacted with hydrobromic acid for about 17 hours at a temperature of about 26° C.

In one embodiment, the Copolymer 1 related peptide is selected from the thirty-two peptides of SEQ ID NO:1-32 (Table 1). The definition of "Cop 1 related-polypeptide" according to the invention is meant to encompass other synthetic amino acid copolymers containing the amino acids phenylalanine, glutamic acid, alanine and lysine (poly FEAK), or tyrosine, phenylalanine, alanine and lysine (poly YFAK), and any other similar copolymer to be discovered that can be considered a universal antigen similar to Cop 1.

According to the present invention, the preferred copolymer for use in the composition of the invention is Copolymer 1, herein referred to also as Cop 1, most preferably in the form of its acetate salt known under the generic name glatiramer acetate. As mentioned before, glatiramer acetate has been approved in several countries for the treatment of multiple sclerosis (MS) and was shown to be well tolerated with only minor side reactions which were mostly mild reactions at the injection site (Johnson et al, 1995).

In accordance with the present invention, Copolymer 1 was tested in $dy^{2j}$ mice, a spontaneously mutated mouse model of merosin-deficient congenital muscular dystrophy.

The $dy^{2j}$ mouse shows continuous relentlessly progressive course of weakness and muscle fibrosis similar to the human clinical course and muscle pathology in this disease.

Cop 1 is also tested on the mdx, a model of Duchenne muscular dystrophy with a point mutation in the dystrophin gene. In contrast to the $dy^{2j}$ model, the mdx mouse model shows early muscle regeneration and spontaneous clinical

TABLE 1

| SEQ ID NO. | Peptide Sequence |
| --- | --- |
| 1 | AAAYAAAAAKAAAA |
| 2 | AEKYAAAAAKAAAA |
| 3 | AKEYAAAAAKAAAA |
| 4 | AKKYAAAAAKAAAA |
| 5 | AEAYAAAAAKAAAA |
| 6 | KEAYAAAAAKAAAA |
| 7 | AEEYAAAAAKAAAA |
| 8 | AAEYAAAAAKAAAA |
| 9 | EKAYAAAAAKAAAA |
| 10 | AAKYEAAAAKAAAA |
| 11 | AAKYAEAAAKAAAA |
| 12 | EAAYAAAAAKAAAA |
| 13 | EKKYAAAAAKAAAA |
| 14 | EAKYAAAAAKAAAA |
| 15 | AEKYAAAAAAAAAA |
| 16 | AKEYAAAAAAAAAA |
| 17 | AKKYEAAAAAAAAA |
| 18 | AKKYAEAAAAAAAA |
| 19 | AEAYKAAAAAAAAA |
| 20 | KEAYAAAAAAAAAA |
| 21 | AEEYKAAAAAAAAA |
| 22 | AAEYKAAAAAAAAA |
| 23 | EKAYAAAAAAAAAA |
| 24 | AAKYEAAAAAAAAA |
| 25 | AAKYAEAAAAAAAA |
| 26 | EKKYAAAAAAAAAA |
| 27 | EAKYAAAAAAAAAA |
| 28 | AEYAKAAAAAAAAA |
| 29 | AEKAYAAAAAAAAA |
| 30 | EKYAAAAAAAAAAA |
| 31 | AYKAEAAAAAAAAA |
| 32 | AKYAEAAAAAAAAA | improvement (Woo et al., 1987; Iannaccone et al., 1995). Gene expression of regeneration: myoD expression indicating satellite cell activation and myogenin expression correlating with myotube appearance are both increased in the mdx while decreased in the $dy^{2j}$ mouse (Jin et al., 2000). Both animal models are accepted as closely resembling the human diseases.

Table 2 depicts the differences between the $dy^{2j}$ and mdx, the two most common mouse models of muscular dystrophy.

TABLE 2

Comparison between the dy$^{2J}$ and the mdx mouse model

| | dy$^{2J}$ | mdx |
|---|---|---|
| Gene mutation | Mutation in the Lama2 gene (chromosome 6q2)-laminin α2 lacking N-terminal domain | Point mutation in the dystrophin gene-lack of dystrophin (X-linked) |
| Development | Decreased body weight compared to controls | Normal |
| Symptoms | From 2-3 weeks of age | Minor from 3 weeks of age |
| Survival | Up to 5-6 month | Up to two years |
| Muscle weakness | Beginning at ~3.5 weeks of age, dragging of the rear limbs | Starting around 3 weeks, mild muscle weakness, spontaneous initial recovery |
| Skeletal muscle necrosis | From day 10 of age | From day 10 of age |
| Regeneration | From day 20 of age | From day 20 of age |
| Fibrosis | skeletal muscles | mainly diaphragm |

According to the present invention, the hind limbs muscle strength of dy$^{2J}$ mice that were given Cop 1 as the active agent by IP injection improved significantly as compared with untreated dy$^{2J}$ mice that were given a placebo. In fact, the treated dy$^{2J}$ mice regained their muscle strength to such an extent that, at the end of the experiment, they were as strong as the wild type mice. Similarly, the mobility of the treated dy$^{2J}$ mice improved significantly upon treatment with Cop 1 as compared with untreated dy$^{2J}$ mice and was at the end of the experiment undistinguishable from the mobility of the wild type mice.

According to the present invention, treatment of muscular dystrophy with Cop 1 is at least as effective as treatment with corticosteroids but without the undesired side effects of the latter.

Although the mechanism of action of corticosteroids in muscular dystrophy is not entirely known, it is well established that corticosteroids have significant anti-inflammatory and immune modulation effect.

The combination of two different active agents effective in the treatment of muscular dystrophy may have an additive or synergistic beneficial effect in the treatment of muscular dystrophy.

Thus, in one embodiment, the active agent or a pharmaceutically acceptable salt thereof is used with at least one anti-inflammatory agent.

The anti-inflammatory agent may be a corticosteroid such as, but not limited to, prednisone, deflazacort and prednisolone.

Other anti-inflammatory agents that may be administered in combination with Cop 1 are the alkaloid colchicine, the standard treatment for gout, and non-steroidal anti-inflammatory drugs (NSAIDs) such as, but not limited to aspirin, choline and magnesium salicylates, choline salicylate, celecoxib, diclofenac, diflunisal, etodolac, fenoprofen calcium, flurbiprofen, ibuprofen, indomethacin, ketoprofen, magnesium salicylate, meclofenamate sodium mefenamic acid, meloxicam, nabumetone, naproxen, oxaprozin, piroxicam, rofecoxib, salsalate, sodium salicylate, sulindac, tolmetin sodium and valdecoxib.

The active agent and the anti-inflammatory agent may be used or administered concomitantly, sequentially, in separate compositions or in a single composition.

In one embodiment, the active agent of the invention, optionally with an anti-inflammatory agent, is used for treating a muscular dystrophy disease or disorder. This disease or disorder refers to a group of genetic, hereditary muscle diseases and disorders causing progressive muscle weakness including Duchenne, Becker, limb girdle, congenital, faciosclapulohumeral, myotonic, oculopharyngeal, distal, and Emery-Dreifuss muscular dystrophy, that are characterized by progressive skeletal muscle weakness, defects in muscle proteins, and the death of muscle cells and tissue. The affected muscles include the diaphragm and the heart muscle and thus the disease in its final stages may lead to congenital heart failure and respiratory failure, which are often the direct cause of death.

The present invention is preferably directed to an active agent for the use in the treatment of Duchenne, limb girdle and congenital muscular dystrophy.

The invention is most preferably directed to an active agent for the use in the treatment of Duchenne muscular dystrophy.

The present invention also provides methods for improving muscle strength and mobility, for preventing or reducing muscle degeneration, fibrosis and/or skeletal scoliosis, preventing congenital heart failure and respiratory failure in a subject with muscular dystrophy disease.

In one aspect, the present invention is directed to the use of an active agent selected from the group consisting of Cop 1, a Cop 1 related-peptide and a Cop 1-related polypeptide, or a pharmaceutically acceptable salt thereof for the preparation of a medicament for the treatment of a muscular dystrophy disease or disorder.

The invention further relates to methods and a pharmaceutical composition for treatment of a muscular dystrophy disease or disorder, comprising a therapeutically effective amount of an active agent selected from the group consisting of Cop 1, a Cop 1 related-peptide and a Cop 1-related polypeptide, or a pharmaceutically acceptable salt thereof.

In a preferred embodiment, the pharmaceutical composition for use in the present invention is administered parenterally. In another preferred embodiment, the pharmaceutical composition for use in the present invention is administered orally.

The invention will now be illustrated by the following non-limiting examples.

EXAMPLES

Materials and Methods

Genotype analysis: The identification of WT (C57BL), HO and heterozygotes for the lama2 gene mutation of the C57BL-Lama 2$^{dy-2J}$ was performed by using PCR reaction with the following primers:

```
Lama2 up (Forward primer):        (SEQ ID NO: 33)
5'-TCC TGC TGT CCT GAA TCT TG-3'

Lama2 low (Reverse p-             (SEQ ID NO: 34)
rimer):
5'- CTC TAT TAC TGA ACT TTG GAT G-3'
```

The digestion of the PCR products with the NdeI restriction enzyme (Fermentas International INC Burlington, Ontario, CANADA) (recognition sequence: CATATG, SEQ ID NO: 35), results in characteristic profiles (Vilquin et al., 2000). The detection of the dy$^{2J}$ allele was performed by using a simple assay, which contains a new NdeI restriction site.

Population: Twenty C57BL old mice were randomly divided into 4 groups (5 in each group):
1. WT mice—treated saline 100 μl/IP
2. WT mice—treated with 200 μg GA/IP
3. HO mice—treated Saline 100 μl/IP
4. HO mice—treated with 200 μg GA/IP At 5 weeks of age WT and dy$^{2J}$ animals were randomly divided to the treated and control groups. The animals were treated three times a week for 13 weeks.

No animal had paralysis with inability to reach food or water or dramatic weight loss (more than 10% weight loss between two weightings or 20% or more than its initial weight) or any other severe stress signs, that would necessitate withdrawal of the animal from the experiment. No other side effects were noted in the treated group.

Measurement of muscle strength (blind measurement). Once a week weight gain and total peak force (in Gram force/g bodyweight) were determined using electronic Grip Strength Meter, Columbus Instruments (Columbus, Ohio). Muscle strength measurements of both fore and hind limbs were performed according to Connolly A. M. et al., 2001. Mice were brought to the testing room and allowed to acclimatize for 10 minutes before the test begins. Five measurements (fore and hind limbs) were taken from each animal. The three highest measurements for each animal were averaged to give the strength score. Between the fore and hind measurements the mice were allowed to rest for 10 minutes. All measurements were performed by the same person.

Motion analysis by video-recording. At the end of the experiment (19 week of age) animal mobility and well-being were video recorded for 10 minutes sessions. The video films were analyzed using the EthoVision system (NBT-New Biotechnology, Jerusalem, Israel, video tracking system recording of activity and movement). Quantitative parameters of mobility of the animals including total distance, maximum distance in 0.2 second, average and peak velocity were calculated.

X ray radiography for scoliosis. Posterior-Anterior X-ray radiography of the mice spine is performed at the end of the study.

Tissue analysis. After 12 weeks of treatment, the animals are sacrificed at the age of 19 weeks and muscle biopsies and blood samples are obtained.

Muscle biopsies. Muscle biopsies were obtained from the hind limbs and were tested for:

1. Muscle histology hematoxylin and eosin stain (H&E) and Gommori trichrome stains
2. Sircol™ Collagen Colorimetric Assay (Biodye science Ltd. N. Ireland) to measure the total muscle collagen content.
3. Western blot and immunohistochemistry for MyoD (Santa Cruz Biotechnology, Inc, California, USA) and myogenin (Santa Cruz Biotechnology, Inc, California, USA)—for assessing muscle regeneration markers.
4. MMPs 2 & 9 activity by Zymography.

Blood samples. Blood samples are obtained for:

1. Creatine phosphokinase (CPK) blood levels—Dry chemistry, Kodak instrument, diagnostic lab Hadassah Hebrew University Hospital, Ein Kerem. Is determined for assessment of integrity of the muscle cells.
2. Cytokines—IL4, IL10, INF-$\gamma$ and TGF-$\beta$-ELISA—Service provided by Prof. Vivian Barak—Hadassah, Hebrew University Hospital, Ein Kerem, Israel. The cytokines are determined for assessment of the immunomodulating effect of the treatment.

Example 1

Figure 1B:
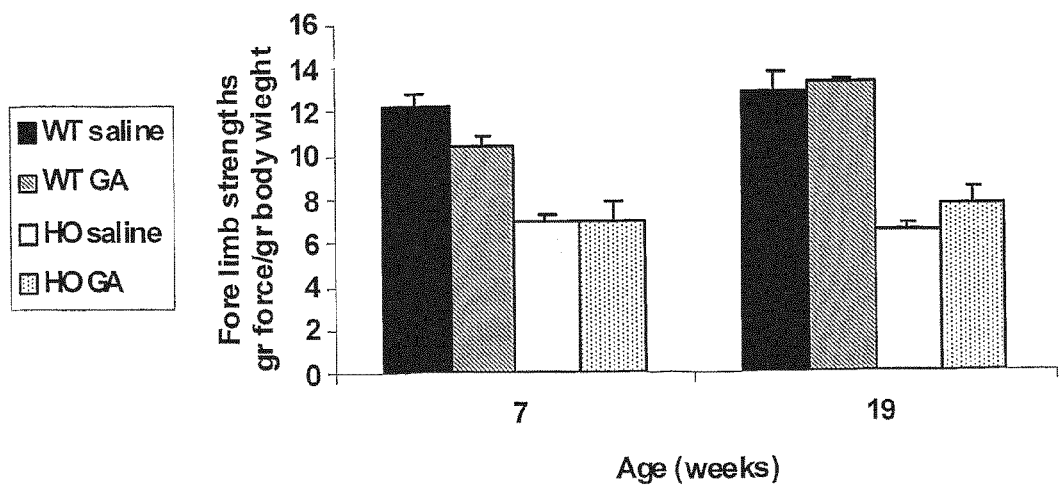

The Effect of GA Treatment on Congenital Muscular Dystrophies in the dy2J Mice Model (i) Muscle strength of hind and fore limbs. Mice were treated with GA or saline as described in Methods. Significant increase in the hind limbs strength between week 7 and week 19 (FIG. 1A) was noted in the GA-treated HO animals compared to the untreated HO group (p=0.0017). There was only minimal effect of GA treatment on the fore (strong) limbs (p=0.13) (FIG. 1B).

Figure 2:
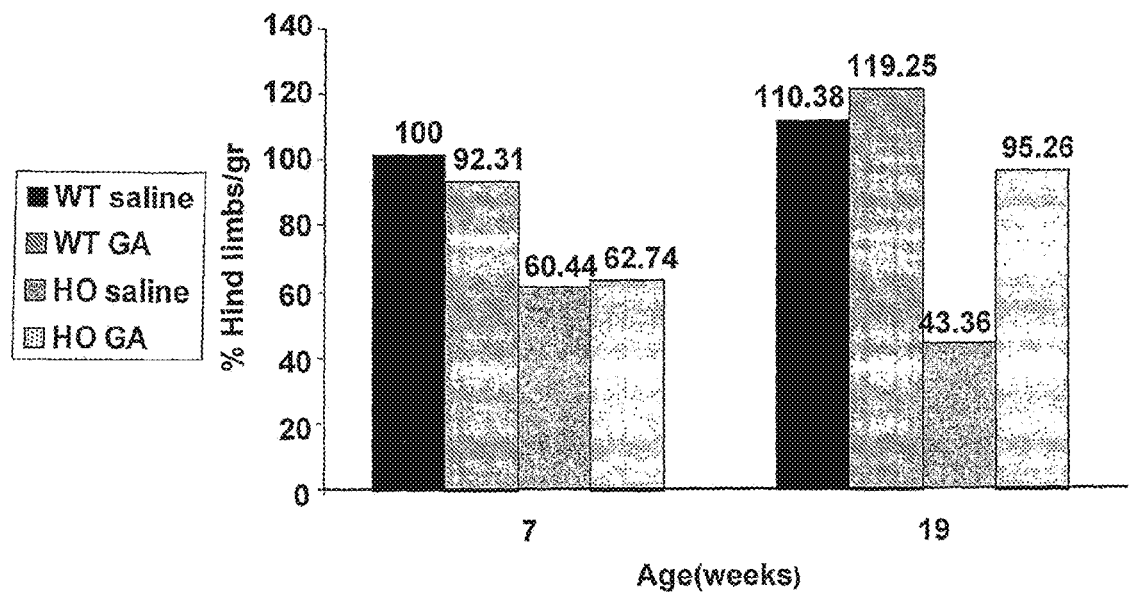
FIG. 2 shows percentage of hind limbs strength of WT and HO mice with and without GA treatment (n=5 for each group). 100% was defined as the strength of the control untreated group (WT saline) at the age of week seven.

The percent of change in the hind limbs muscle strength (gram force) between the onset and the end of the study is shown in FIG. 2. The average strength of the untreated control group (WT saline) at the age of seven weeks was defined as 100%. The initial strength (at week 7) of HO untreated group was 60.44%. It decreased to 43.36% at the end of the study (age 19 weeks). The strength of HO treated mice was 62.74% initially and increased to 95.26% at the end of the experiment.

Figure 3:
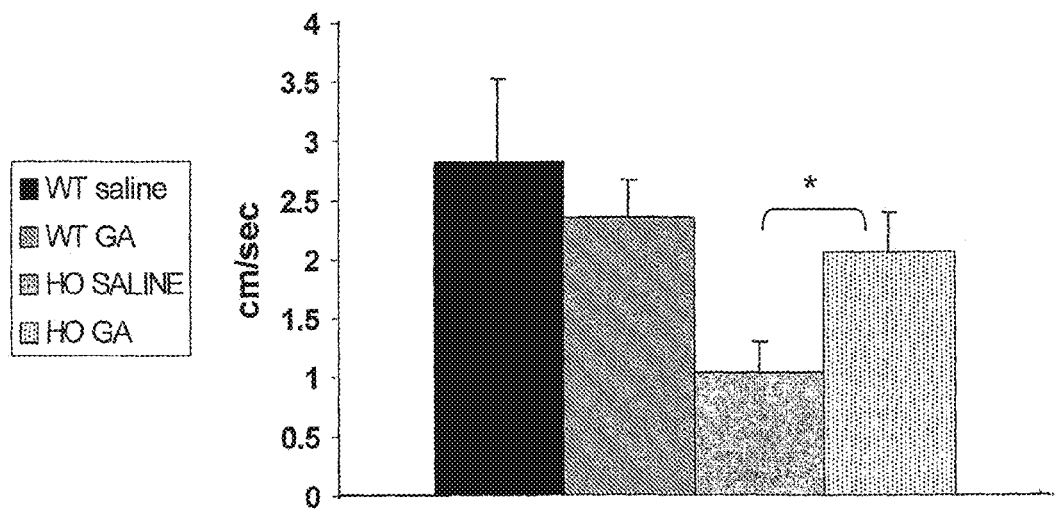
FIG. 3 shows "ten minutes velocity" of the GA-treated and untreated WT and HO mice at the end of the treatment period.

(ii) Mobility. Mice from all groups (WT saline; n=2, WT GA; n=4, HO saline; n=4, HO GA; n=5) were video-recorded for 10 minutes sessions. Total ten minutes average velocity as calculated with the Ethovision system was significantly faster in the HO GA-treated mice compared to the untreated mice (p=0.051) and not significantly different in the WT groups (p=0.51) (FIG. 3).

Figure 4:
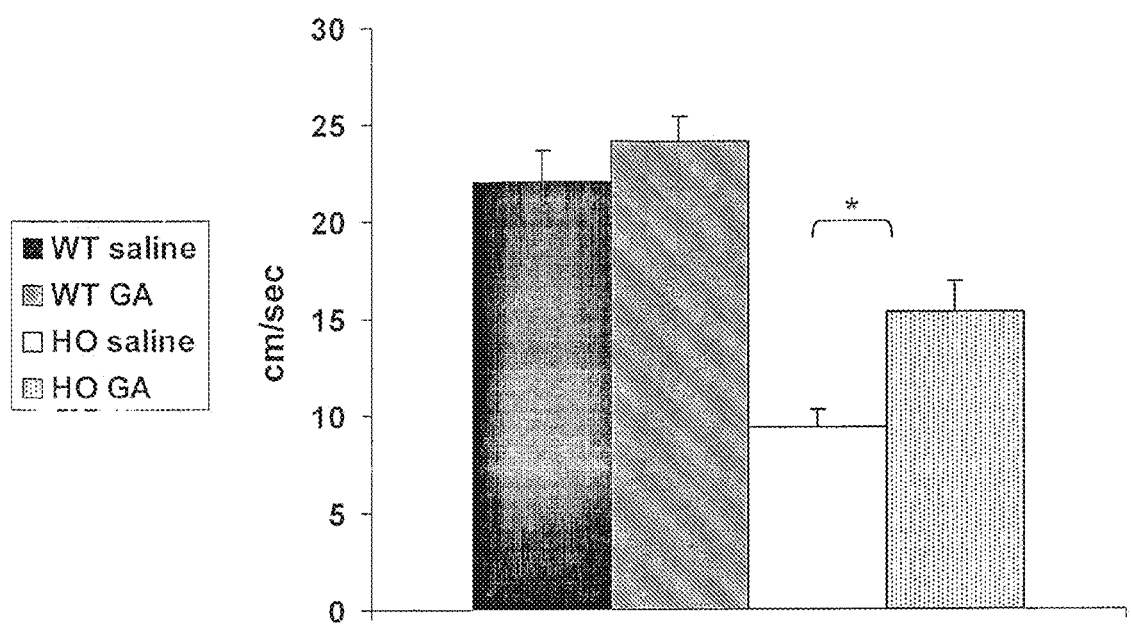
FIG. 4 depicts maximal velocity in 0.2 sec period of the GA-treated and untreated WT and HO mice at the end of the treatment period.

The 10-minutes sessions were divided into 0.2-second measurements. The peak velocity in 0.2 sec period examined was significantly faster in the HO GA-treated mice compared to the HO untreated group (p=0.017) and was not significantly different in the WT groups (p=0.38) (FIG. 4).

Figure 5:
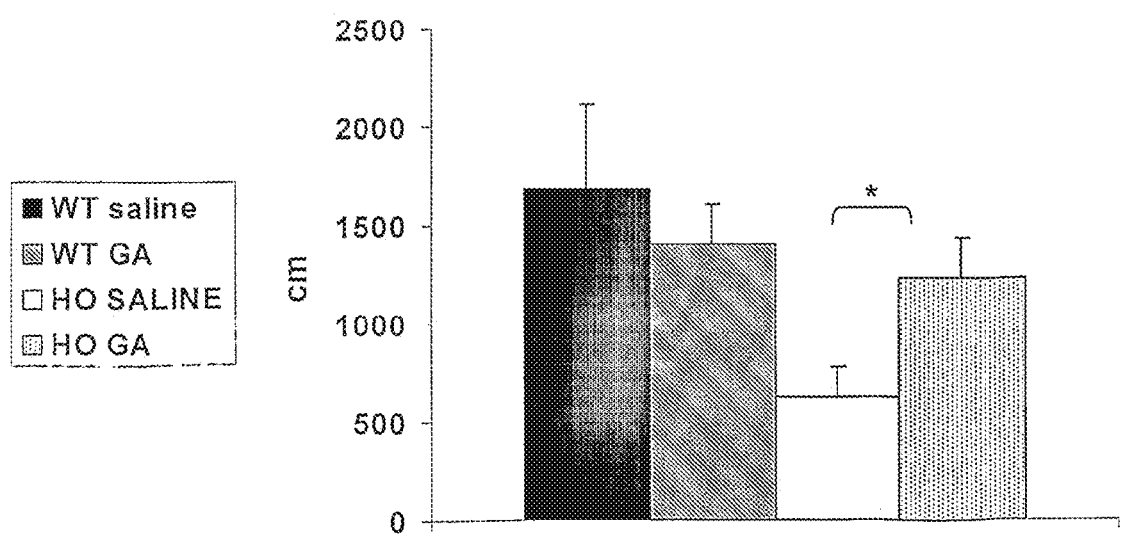
FIG. 5 shows "ten minutes total distance" of the GA-treated and untreated WT and HO mice at the end of the treatment period.

Total 10-minutes average distance as calculated with the Ethovision system was significantly longer in the HO GA treated mice compared to the untreated group (p=0.052) and was not significantly different in the WT groups (p=0.51) (FIG. 5).

Figure 6:
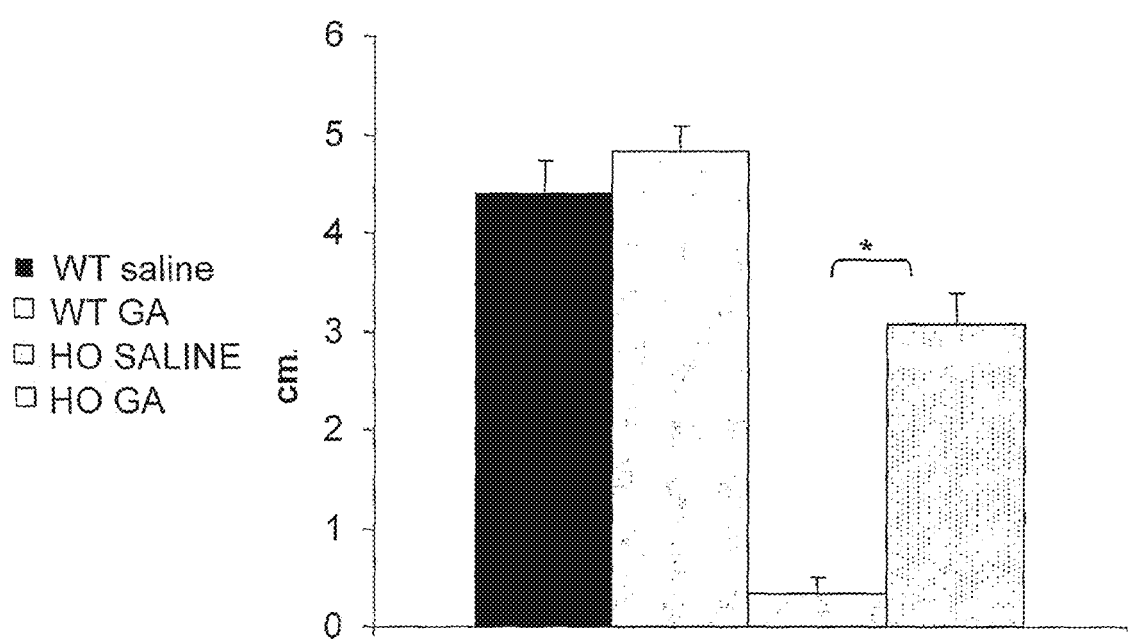
FIG. 6 shows maximal velocity in 0.2 sec period of the GA-treated and untreated WT and HO mice at the end of the treatment period.

The maximal distance in 0.2 sec period for the total 10 min that were examined as obtained by the Ethovision system was significantly longer in the HO GA treated compared to the untreated mice (p=0.016) and was not significantly different in the WT groups (p=0.39) (FIG. 6).

Figure 7A:
FIGS. 7A-B show muscle biopsies from (A) $dy^{2j}$ dystrophic untreated mice and (B) $dy^{2j}$ dystrophic mice treated with GA for 12 weeks. The biopsies are stained with Hematoxylin-Eosin dye.
Figure 7B:
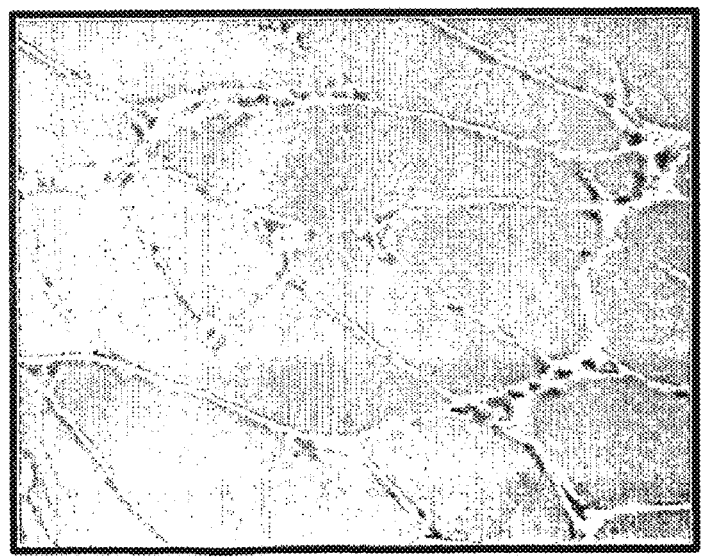

(iii) Muscular fibrosis. Hematoxylin-Eosin dye of muscle biopsies taken from $dy^{2j}$ mice in week 17 significantly reduced muscular fibrosis in mice treated with GA for 12 weeks (FIG. 7B) as compared with untreated mice (FIG. 7A)

Example 2

The Effect of GA Treatment on Congenital Muscular Dystrophies in the mdx Mice Model The positive results of the preliminary studies in the $dy^{2j}$ encouraged us to extend the study to the mdx mouse model of DMD to evaluate the potential therapeutic effect of GA on the mdx mice and to evaluate different doses to find the optimal effect.

The experiments described in Example 1 above is repeated but the $dy^{2j}$ mice is replaced with mdx mice. Ten WT C57BL mice and ten mdx mice are divided into four groups with five mice in each group: WT C57BL treated and untreated; and mdx treated and untreated mice. The experiment is duplicated; half the mice are tested after twice weekly treadmill running of 20 minutes (EXER-6M open treadmill for mice, Columbus instruments). Altogether the population consists of 40 mdx mice. Evaluation will be for up to 8 months Muscle strength of hind and fore limbs, X ray for scoliosis, tissue analysis, muscle biopsies and blood levels of CPK and cytokines are all measured as described above in Materials and Methods.

Example 3

Different Regimes of GA Administration to the $dy^{2j}$ and mdx Mice and of Administration of a Combination of Corticosteroids and GA to $dy^{2j}$ and mdx Models Population: Wild type C57BL mice, $dy^{2j}$ and mdx mice.

Treatment A. Different doses of GA are injected intraperitoneally every 3 weeks. Evaluation is for up to 8 months.

Treatment B. Different doses of GA and corticosteroids are administered every 3 weeks. Ga is injected intraperitoneally and the corticosteroids are given orally; however, alternatively the corticosteroids may also be injected intraperitoneally. GA and the corticosteroid may be administered simultaneously, practically simultaneously at the same treatment occasion or sequentially. The corticosteroids evaluated are prednisone, prednisolone and deflazacort. Evaluation is for up to 8 months.

Primary outcome measures. The clinical effect of GA compared to placebo (saline).
  A. Muscle strength measurements by grip strength meter with and without treadmill exercise.
  B. Mouse mobility analyzed by Etho Vision software.
  C. Skeletal scoliosis evaluated by X-ray.

Secondary outcome measures. Muscle degeneration, fibrosis and regeneration parameters (for details see methods; Both limb and diaphragm muscles are obtained):
  A. Muscle degeneration, regeneration and fibrosis evaluated by muscle pathology.
  B. Muscle degeneration by CPK level determination.
  C. Inflammation assessed by quantitative inflammatory cytokines analysis.
  D. Fibrosis by quantitative tissue collagen measurement.
  E. Regeneration by immunostaining for regeneration markers.

The potential role of a medication with immune modulating effects and significantly lower side effects than those of corticosteroids, in muscular dystrophy is enormous. Moreover, GA may be given in addition to corticosteroids with potential synergy.

REFERENCES

Aharoni R, Schlegel P G, Teitelbaum D, Roikhel-Karpov O, Chen Y, Arnon R, Sela M, Chao N J. Studies on the mechanism and specificity of the effect of the synthetic random copolymer GLAT on graft-versus-host disease. Immunol Lett. 1997 July; 58(2):79-87.

Aharoni R, Teitelbaum D, Arnon R, Sela M. Copolymer 1 acts against the immunodominant epitope 82-100 of myelin basic protein by T cell receptor antagonism in addition to major histocompatibility complex blocking. Proc Natl Acad Sci USA. 1999 Jan. 19; 96(2):634-9.

Aharoni R, Teitelbaum D, Arnon R, Sela M. Copolymer 1 inhibits manifestations of graft rejection. Transplantation. 2001 Aug. 27; 72(4):598-605.

Angelini C. The role of corticosteroids in muscular dystrophy: A critical appraisal. Muscle Nerve. 2007 May 31; [Epub ahead of print]

Biton Y, Reif S, Chapman Y, Nevo Y. The effect of FTS a unique RAS antagonist on fibrosis and progression of weakness in the DY2J mouse. Neuromuscul Disord, 16(S1):S55, 2006.

Connolly A M, Keeling R M, Mehta S, Pestronk A, Sanes J R. Three mouse models of muscular dystrophy: the natural history of strength and fatigue in dystrophin-, dystrophin/utrophin-, and laminin alpha2-deficient mice. Neuromuscul Disord. 2001 November; 11(8):703.12

Dalkilic I, Kunkel L M. Muscular dystrophies: genes to pathogenesis. Curr Opin Genet Dev. 2003 June; 13(3):231-8.

Farina C, Weber M S, Meinl E, Wekerle H, Hohlfeld R. Glatiramer acetate in multiple sclerosis: update on potential mechanisms of action. Lancet Neurol. 2005 September; 4(9):567-75.

Ge Y, Molloy M P, Chamberlain J S, Andrews P C. Differential expression of the skeletal muscle proteome in mdx mice at different ages. Electrophoresis. 2004 August; 25(15):2576-85.

Hussein M R, Hamed S A, Mostafa M G, Abu-Dief E E, Kamel N F, Kandil M R. The effects of glucocorticoid therapy on the inflammatory and dendritic cells in muscular dystrophies. Int J Exp Pathol. 2006 December; 87(6): 451-61.

Iannaccone S, Quattrini A, Smirne S, Sessa M, de Rino F, Ferini-Strambi L, Nemni R. Connective tissue proliferation and growth factors in animal models of Duchenne muscular dystrophy. J Neurol Sci. 1995 January; 128(1): 36-44.

Jin Y, Murakami N, Saito Y, Goto Y, Koishi K, Nonaka I. Expression of MyoD and myogenin in dystrophic mice, mdx and dy, during regeneration. Acta Neuropathol (Berl). 2000 June; 99(6):619-27.

Johnson et al. (1995) "Copolymer 1 reduces relapse rate and improves disability in relapsing-remitting multiple sclerosis: results of a phase III multicenter, double-blind placebo-controlled trial. The Copolymer 1 Multiple Sclerosis Study Group," Neurology 1:65

Keeling R M, Golumbek P T, Streif E M, Connolly A M. Weekly oral prednisolone improves survival and strength in male mdx mice. Muscle Nerve. 2007; 35(1):43-8.

Kissel J T, Lynn D J, Rammohan K W, Klein J P, Griggs R C, Moxley R T, Cwik V A, Brooke M H, Mendell J R. Mononuclear cell analysis of muscle biopsies in prednisone- and azathioprine-treated Duchenne muscular dystrophy. Neurology. 1993; 43(3 Pt 1):532-6.

Manzur A Y, Kuntzer T, Pike M, Swan A. Glucocorticoid corticosteroids for Duchenne muscular dystrophy. Cochrane Database Syst Rev. 2004; (2):CD003725.

Matthys P, Vermeire K, Billiau A. Mac-1(+) myelopoiesis induced by CFA: a clue to the paradoxical effects of IFN-gamma in autoimmune disease models. Trends Immunol. 2001; 22(7):367-71.

Matthys P, Vermeire K, Mitera T, Heremans H, Huang S, Schols D, De Wolf-Peeters C, Billiau A. Enhanced autoimmune arthritis in IFN-gamma receptor-deficient mice is conditioned by mycobacteria in Freund's adjuvant and by increased expansion of Mac-1+ myeloid cells. J Immunol. 1999; 163(6):3503-10.

Miller A, Shapiro S, Gershtein R, Kinarty A, Rawashdeh H, Honigman S, Lahat N. Treatment of multiple sclerosis with copolymer-1 (Copaxone): implicating mechanisms of Th1 to Th2/Th3 immune-deviation. J Neuroimmunol. 1998 Dec. 1; 92(1-2):113-21.

Morrison J, Lu Q L, Pastoret C, Partridge T, Bou-Gharios G. T-cell-dependent fibrosis in the mdx dystrophic mouse. Lab Invest. 2000; 80(6):881-91.

Morrison J, Palmer D B, Cobbold S, Partridge T, Bou-Gharios G. Effects of T-lymphocyte depletion on muscle fibrosis in the mdx mouse. Am J Pathol. 2005; 166(6):1701-10.

Nevo Y. Anti fibrotic medications in muscular dystrophy. Neuromuscul Disord, 16(S1):S193, 2006.

Petrof B J, Shrager J B, Stedman H H, Kelly A M, Sweeney H L. Dystrophin protects the sarcolemma from stresses developed during muscle contraction. Proc Natl Acad Sci USA. 1993; 90(8):3710-4.

Putheti P, Soderstrom M, Link H, Huang Y M. Effect of glatiramer acetate (Copaxone) on CD4+CD25 high T regulatory cells and their IL-10 production in multiple sclerosis. J Neuroimmunol. 2003 November; 144(1-2):125-31.

Spencer M J, Tidball J G. Do immune cells promote the pathology of dystrophin-deficient myopathies? Neuromuscul Disord. 2001; 11(6-7):556-64.

Tidball J G, Wehling-Henricks M. Damage and inflammation in muscular dystrophy: potential implications and relationships with autoimmune myositis. Curr Opin Rheumatol. 2005; 17(6):707-13.

Tran E H, Prince E N, Owens T. IFN-gamma shapes immune invasion of the central nervous system via regulation of chemokines. J Immunol. 2000; 164(5):2759-68.

Vilquin J T, Vignier N, Tremblay J P, Engvall E, Schwartz K, Fiszman M. Identification of homozygous and heterozygous dy2J mice by PCR. Neuromuscul Disord. 10:59-62, 2000.

Wehling M, Spencer M J, Tidball J G. A nitric oxide synthase transgene ameliorates muscular dystrophy in mdx mice. J Cell Biol. 2001; 155(1):123-31.

Woo M, Tanabe Y, Ishii H, Nonaka I, Yokoyama M, Esaki K. Muscle fiber growth and necrosis in dystrophic muscles: a comparative study between dy and mdx mice. J Neurol Sci. 1987; 82(1-3):111-22.

The invention claimed is:

1. A method for treating a muscular dystrophy disease or disorder, comprising administering to a subject in need a therapeutically effective amount of Copolymer 1 or a pharmaceutically acceptable salt thereof as the sole medicament.

2. The method according to claim 1, wherein said Copolymer 1, or a pharmaceutically acceptable salt thereof, is for use in combination with at least one anti-inflammatory agent as the further sole medicaments.

3. The method according to claim 2, wherein said anti-inflammatory agent is a corticosteroid, a non-steroid anti-inflammatory drug or colchicine.

4. The method according to claim 3, wherein said corticosteroid is prednisone, prednisolone or deflazacort.

5. The method according to claim 2, wherein said Copolymer 1 or a pharmaceutically acceptable salt thereof and said anti-inflammatory agent are for concomitant administration.

6. The method according to claim 2, wherein said Copolymer 1 or a pharmaceutically acceptable salt thereof and said anti-inflammatory agent are for sequential administration.

7. The method according to claim 2, wherein said Copolymer 1 or a pharmaceutically acceptable salt thereof and said anti-inflammatory agent are in separate compositions.

8. The method according to claim 2, wherein said Copolymer 1 or a pharmaceutically acceptable salt thereof and said anti-inflammatory agent are in a single composition.

9. The method according to claim 1, wherein said muscular dystrophy disease is selected from the group consisting of Duchenne, Becker, limb girdle, congenital, facioscapulohumeral, myotonic, oculopharyngeal, distal, and Emery-Dreifuss muscular dystrophy.

10. The method according to claim 9, wherein said muscular dystrophy disease is Duchenne muscular dystrophy.

11. The method according to claim 9, wherein said muscular dystrophy disease is limb girdle or congenital muscular dystrophy.

12. The method according to claim 1, wherein said treatment causes improvement of muscle strength and mobility.

13. The method according to claim 1, wherein said treatment reduces muscle degeneration, fibrosis and/or skeletal scoliosis.

14. The method according to claim 1, wherein said treatment reduces congenital heart failure or respiratory failure.

* * * * *

SEQUENCE LISTING

```
<160> NUMBER OF SEQ ID NOS: 35

<210> SEQ ID NO 1
<211> LENGTH: 15
<212> TYPE: PRT
<213> ORGANISM: Artificial Sequence
<220> FEATURE:
<223> OTHER INFORMATION: Synthetic peptide

<400> SEQUENCE: 1

Ala Ala Ala Tyr Ala Ala Ala Ala Ala Ala Lys Ala Ala Ala Ala
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Synthetic peptide

<400> SEQUENCE: 2

Ala Glu Lys Tyr Ala Ala Ala Ala Ala Ala Lys Ala Ala Ala Ala
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Synthetic peptide

<400> SEQUENCE: 3

Ala Lys Glu Tyr Ala Ala Ala Ala Ala Ala Lys Ala Ala Ala Ala
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Synthetic peptide

<400> SEQUENCE: 4

Ala Lys Lys Tyr Ala Ala Ala Ala Ala Ala Lys Ala Ala Ala Ala
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Synthetic peptide

<400> SEQUENCE: 5

Ala Glu Ala Tyr Ala Ala Ala Ala Ala Ala Lys Ala Ala Ala Ala
1               5                   10                  15
```

```
<210> SEQ ID NO 6
<211> LENGTH: 15
<212> TYPE: PRT
<213> ORGANISM: Artificial Sequence
<220> FEATURE:
<223> OTHER INFORMATION: Synthetic peptide

<400> SEQUENCE: 6

Lys Glu Ala Tyr Ala Ala Ala Ala Ala Lys Ala Ala Ala Ala
 1               5                  10                  15

<210> SEQ ID NO 7
<211> LENGTH: 15
<212> TYPE: PRT
<213> ORGANISM: Artificial Sequence
<220> FEATURE:
<223> OTHER INFORMATION: Synthetic peptide

<400> SEQUENCE: 7

Ala Glu Glu Tyr Ala Ala Ala Ala Ala Ala Lys Ala Ala Ala Ala
 1               5                  10                  15

<210> SEQ ID NO 8
<211> LENGTH: 15
<212> TYPE: PRT
<213> ORGANISM: Artificial Sequence
<220> FEATURE:
<223> OTHER INFORMATION: Synthetic peptide

<400> SEQUENCE: 8

Ala Ala Glu Tyr Ala Ala Ala Ala Ala Lys Ala Ala Ala Ala
 1               5                  10                  15

<210> SEQ ID NO 9
<211> LENGTH: 15
<212> TYPE: PRT
<213> ORGANISM: Artificial Sequence
<220> FEATURE:
<223> OTHER INFORMATION: Synthetic peptide

<400> SEQUENCE: 9

Glu Lys Ala Tyr Ala Ala Ala Ala Ala Lys Ala Ala Ala Ala
 1               5                  10                  15

<210> SEQ ID NO 10
<211> LENGTH: 15
<212> TYPE: PRT
<213> ORGANISM: Artificial Sequence
<220> FEATURE:
<223> OTHER INFORMATION: Synthetic peptide

<400> SEQUENCE: 10

Ala Ala Lys Tyr Glu Ala Ala Ala Ala Lys Ala Ala Ala Ala
 1               5                  10                  15

<210> SEQ ID NO 11
<211> LENGTH: 15
<212> TYPE: PRT
<213> ORGANISM: Artificial Sequence
<220> FEATURE:
<223> OTHER INFORMATION: Synthetic peptide

<400> SEQUENCE: 11

Ala Ala Lys Tyr Ala Glu Ala Ala Ala Lys Ala Ala Ala Ala
 1               5                  10                  15
```

```
<210> SEQ ID NO 12
<211> LENGTH: 15
<212> TYPE: PRT
<213> ORGANISM: Artificial Sequence
<220> FEATURE:
<223> OTHER INFORMATION: Synthetic peptide

<400> SEQUENCE: 12

Glu Ala Ala Tyr Ala Ala Ala Ala Ala Lys Ala Ala Ala Ala
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Synthetic peptide

<400> SEQUENCE: 13

Glu Lys Lys Tyr Ala Ala Ala Ala Ala Lys Ala Ala Ala Ala
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Synthetic peptide

<400> SEQUENCE: 14

Glu Ala Lys Tyr Ala Ala Ala Ala Ala Lys Ala Ala Ala Ala
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Synthetic peptide

<400> SEQUENCE: 15

Ala Glu Lys Tyr Ala Ala Ala Ala Ala Ala Ala Ala Ala Ala
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Synthetic peptide

<400> SEQUENCE: 16

Ala Lys Glu Tyr Ala Ala Ala Ala Ala Ala Ala Ala Ala Ala
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Synthetic peptide

<400> SEQUENCE: 17

Ala Lys Lys Tyr Glu Ala Ala Ala Ala Ala Ala Ala Ala Ala
1               5                   10                  15
```

```
<210> SEQ ID NO 18
<211> LENGTH: 15
<212> TYPE: PRT
<213> ORGANISM: Artificial Sequenece
<220> FEATURE:
<223> OTHER INFORMATION: Synthetic peptide

<400> SEQUENCE: 18

Ala Lys Lys Tyr Ala Glu Ala Ala Ala Ala Ala Ala Ala Ala Ala
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Synthetic peptide

<400> SEQUENCE: 19

Ala Glu Ala Tyr Lys Ala Ala Ala Ala Ala Ala Ala Ala Ala Ala
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Synthetic peptide

<400> SEQUENCE: 20

Lys Glu Ala Tyr Ala Ala Ala Ala Ala Ala Ala Ala Ala Ala Ala
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Synthetic peptide

<400> SEQUENCE: 21

Ala Glu Glu Tyr Lys Ala Ala Ala Ala Ala Ala Ala Ala Ala Ala
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Synthetic peptide

<400> SEQUENCE: 22

Ala Ala Glu Tyr Lys Ala Ala Ala Ala Ala Ala Ala Ala Ala Ala
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Synthetic peptide

<400> SEQUENCE: 23

Glu Lys Ala Tyr Ala Ala Ala Ala Ala Ala Ala Ala Ala Ala Ala
1               5                   10                  15
```

```
<210> SEQ ID NO 24
<211> LENGTH: 15
<212> TYPE: PRT
<213> ORGANISM: Artificial Sequence
<220> FEATURE:
<223> OTHER INFORMATION: Synthetic peptide

<400> SEQUENCE: 24

Ala Ala Lys Tyr Glu Ala Ala Ala Ala Ala Ala Ala Ala Ala Ala
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Synthetic peptide

<400> SEQUENCE: 25

Ala Ala Lys Tyr Ala Glu Ala Ala Ala Ala Ala Ala Ala Ala Ala
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Synthetic peptide

<400> SEQUENCE: 26

Glu Lys Lys Tyr Ala Ala Ala Ala Ala Ala Ala Ala Ala Ala Ala
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Synthetic peptide

<400> SEQUENCE: 27

Glu Ala Lys Tyr Ala Ala Ala Ala Ala Ala Ala Ala Ala Ala Ala
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Synthetic peptide

<400> SEQUENCE: 28

Ala Glu Tyr Ala Lys Ala Ala Ala Ala Ala Ala Ala Ala Ala Ala
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Synthetic peptide

<400> SEQUENCE: 29

Ala Glu Lys Ala Tyr Ala Ala Ala Ala Ala Ala Ala Ala Ala Ala
1               5                   10                  15
```

```
<210> SEQ ID NO 30
<211> LENGTH: 15
<212> TYPE: PRT
<213> ORGANISM: Artificial Sequence
<220> FEATURE:
<223> OTHER INFORMATION: Synthetic peptide

<400> SEQUENCE: 30

Glu Lys Tyr Ala Ala Ala Ala Ala Ala Ala Ala Ala Ala Ala Ala
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Synthetic peptide

<400> SEQUENCE: 31

Ala Tyr Lys Ala Glu Ala Ala Ala Ala Ala Ala Ala Ala Ala Ala
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Synthetic peptide

<400> SEQUENCE: 32

Ala Lys Tyr Ala Glu Ala Ala Ala Ala Ala Ala Ala Ala Ala Ala
1               5                   10                  15

<210> SEQ ID NO 33
<211> LENGTH: 20
<212> TYPE: DNA
<213> ORGANISM: Artificial
<220> FEATURE:
<223> OTHER INFORMATION: synthetic

<400> SEQUENCE: 33
tcctgctgtc ctgaatcttg                                              20

<210> SEQ ID NO 34
<211> LENGTH: 21
<212> TYPE: DNA
<213> ORGANISM: Artificial
<220> FEATURE:
<223> OTHER INFORMATION: synthetic

<400> SEQUENCE: 34
ctctattact gaactttgga t                                            21

<210> SEQ ID NO 35
<211> LENGTH: 6
<212> TYPE: DNA
<213> ORGANISM: Artificial
<220> FEATURE:
<223> OTHER INFORMATION: synthetic

<400> SEQUENCE: 35 catatg                                                              6
```